(12) United States Patent
Godschalx et al.

(10) Patent No.: US 8,044,214 B2
(45) Date of Patent: Oct. 25, 2011

(54) PROCESS FOR PREPARING ISOXAZOLE COMPOUNDS

(75) Inventors: James P. Godschalx, Midland, MI (US); G. David Green, Cary, IL (US)

(73) Assignees: ANGUS Chemical Company, Buffalo Grove, IL (US); Dow Global Technologies LLC, Midland, MI (US)

( * ) Notice: Subject to any disclaimer, the term of this patent is extended or adjusted under 35 U.S.C. 154(b) by 268 days.

(21) Appl. No.: 12/539,681

(22) Filed: Aug. 12, 2009

(65) Prior Publication Data
US 2010/0048910 A1 Feb. 25, 2010

Related U.S. Application Data

(60) Provisional application No. 61/091,528, filed on Aug. 25, 2008.

(51) Int. Cl.
*C07D 261/18* (2006.01)
(52) U.S. Cl. ...................................... 548/248
(58) Field of Classification Search .................. None
See application file for complete search history.

(56) References Cited

U.S. PATENT DOCUMENTS
3,466,296 A 9/1969 Plemmons et al.

OTHER PUBLICATIONS

Shimizu et al., "The Reaction of Primary Nitro Compounds with Dipolarophiles in the Presence of p- Toluenesulfonic Acid", Bull. Chem. Soc. Jpn., 1984, 2531-2534, vol. 57.
Shimizu et al., "A Convenient Preparative Method of Nitrile Oxides by the Dehydration of Primary Nitro Compounds with Ethyl Chloroformate or Benzenesulfonyl Chloride in the Presence of Triethylamine", Bull. Chem. Soc. Jpn., 1986, 2827-2831, vol. 99.
Basel et al., "An Improved Method for Preparation of Nitrile Oxides from Nitroalkanes for In Situ Dipolar Cycloadditions", Synthesis, 1997, 309-312.
Kurkowska et al., "Utilisation of enols of mono- and dicarbonyls compounds in 1,3-dipolar cycloaddition reactions", J. Chem. Research (S), 2003, 254-255.
Bachman et al., "Derivatives of Primary Nitroalkanes Preparation of Isoxazolines", J. Org. Chem., 1962, 1150-1152, vol. 28.
Maugein et al., "New Conditions for the Generation of Nitrile Oxides from Primary Nitroalkanes", Tetrahedron Letters, 1997, 1547-1550, vol. 38, No. 9.
McKillop et al., "An Investigation of the Reaction of Primary Nitroalkanes with Acetic Anhydride/Sodium Acetate", Tetrahedron, 1974, 1365-1371, vol. 30.
Cecchi et al., "Isoxazoline derivatives from activated primary nitrocompounds and tertiary diamines", Tetrahedron Letters, 2005, 7877-7879, vol. 46, Elsevier Ltd.
Larsen et al., "An Improved Procedure for the Preparation of 2-Isoxazolines", Tetrahedron, 1984, 2985-2988, vol. 40 No. 15.
Xin et al., "Synthesis and structure-activity relationships of isoxazole carboxamides as growth hormone secretagogue receptor antagonists", Bioorganic & Medicinal Chemistry Letters, 2005, 1201-1204, vol. 15.
Maloney et al., "Identification of a Chemical Tool for the Orphan Nuclear Receptor FXR", Journal of Medicinal Chemistry, 2000, 2971-2974, vol. 43 No. 16.
Maloney et al, "Identification of Chemical Tool for the Orphan Nuclear Receptor FXR", J. Med. Chem., 2000, 1-6 (Supporting Information).
Takikawa et al. "Synthesis of Highly Functionalized Isoxazoles via Base-Promoted Cyclocondensation of Stable Nitrile Oxides with Active Methylene Compounds", Tokyo Institute of Technology, Synlett 2007, 2252-2256, No. 14.
Hydorn et al., "Synthesis and Characterization of Isomeric Methylphenylisoxazole-4-carboxylic Acids", The Squibb Institute for Medical Research, J. Org. Chem., 1962, 4305-4309.
Weimin et al., "Convenient Synthesis of 5-perfluoralkylsubstituted isoxazoles", Tetrahedron, 2001, 5781-5784, vol. 57, Elsevier Science Ltd.
Burdett et al., "Keto-Enol Tautomerism in B-Dicarbonyls Studied by Nuclear Magnetic Resonance Spectroscopy. I. Proton Chemical Shifts and Equilibrium Constants of Pure Compounds", Kedzie Chemical Laboratory, J. Am. Chem. Soc., 1964, 2105-2109, vol. 86.
Mukaiyama et al., "The Reactions of Primary Nitroparaffins with Isocyanates", Tokyo Institute of Technology, J. Am. Chem. Soc., 1960, 5339-5342, vol. 82.
Jones et al., "A Cycloaddition Approach to 3-Acyltetramic and 3-Acyltetronic Acids", J. Chem. Soc. Perkin Trans., 1994, 2513-2515, vol. 1.
Datacase CA [online] Chemical Abstract Services, 5-Methyl-3-phenylisoxazole-4-carboxylates, XP-002550775 for JP 44018296.
International Search Report and Written Opinion for PCT/US2009/053508 dated Oct. 27, 2009.

*Primary Examiner* — Kamal Saeed

(57) ABSTRACT

A process for preparing isoxazole compounds of formula I:

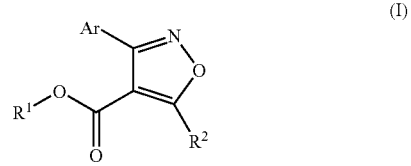

in which a nitroaryl of the formula (II):

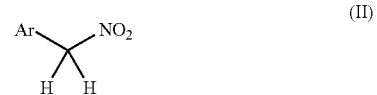

is contacted with an alkyl acetoacetate of the formula (III) or a salt thereof:

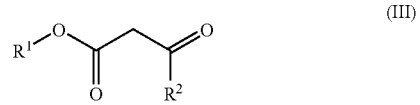

in the presence of an activating agent and a base to provide the isoxazole compound.

6 Claims, No Drawings

PROCESS FOR PREPARING ISOXAZOLE COMPOUNDS

This application claims priority to U.S. provisional application Ser. No. 61/091,528, filed Aug. 25, 2008, which is incorporated herein by reference in its entirety.

FIELD OF THE INVENTION

The invention relates to a process for preparing isoxazole compounds. More particularly, the process utilizes nitroaryls and alkyl acetoacetates as starting materials.

BACKGROUND OF THE INVENTION

Isoxazole compounds, such as those of formula I described below, are useful intermediates in the synthesis of a variety of products, including antibiotics and other pharmaceutical compounds, agricultural chemicals, dye compounds, etc.

Isoxazole compounds can be prepared, for example, from hydroximoyl halides via intermediate formation of a nitrile oxide. This process requires multiple steps and requires potentially expensive reagents. Desirable, therefore, is a more direct route for the synthesis of isoxazoles.

BRIEF SUMMARY OF THE INVENTION

The invention provides a process for making isoxazole compounds that is simpler and more economical than previously known processes. The process comprises: contacting a nitroaryl of the formula (II):

with an alkyl acetoacetate of the formula (III) or a salt thereof:

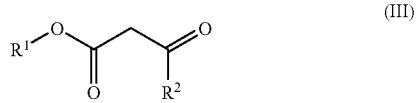

in the presence of an activating agent and a base, under conditions sufficient to provide an isoxazole compound of formula (I):

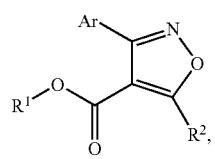

wherein

Ar is phenyl, naphthyl, or biphenyl, each of which is optionally substituted with 1, 2, or 3 groups independently selected from methyl, chloro, bromo, fluoro, iodo and trifluoromethyl;

$R^1$ is $C_1$-$C_8$ alkyl or cycloalkyl; and $R^2$ is $C_1$-$C_{12}$ alkyl, cycloalkyl, aryl, or aryl-$C_1$-$C_{12}$-alkyl-, each of which is optionally substituted with halogen or trifluoromethyl.

DETAILED DESCRIPTION OF THE INVENTION

As noted above, the invention provides a process for preparing isoxazole compounds of formula I. According to the process, a nitroaryl compound of formula II is reacted with an alkyl acetoacetate of formula III in the presence of an activating agent and a base. The reaction may be conducted in a solvent. Preferably, the mole ratio of the arylnitromethane to the activating agent is about 1:1. The preferred mole ratio of arylnitromethane to alkyl acetoacetate is also 1:1 although an excess or deficiency of alkyl acetoacetate may be used. Preferably the alkyl acetoacetate is used as a metal salt (e.g., sodium salt) when reacted with the arylnitromethane. The salt can be added as a premade material or may be prepared in-situ. The salt form functions both as alkyl acetoacetate and as base, therefore no separate addition of base is required. However, even when an alkyl acetoacetate salt is used, use of additional base is desirable. Preferably, a mixture of the arylnitromethane and activating agent is added to a solution of the alkyl acetoacetate and base in a solvent. Alternatively, the base may be added to a mixture of all other components in a solvent.

By way of example, a typical procedure for carrying out the process of the invention is as follows. The alkyl acetoacetate of formula III and a base are dissolved or dispersed in a solvent in a suitable reaction vessel under inert atmosphere. A solution or dispersion of the nitroaryl and activating agent (each preferably equimolar to the alkyl acetoacetate), in a solvent, is slowly added to the alkyl acetoacetate, such as by syringe, addition funnel, or the like, again under inert atmosphere and with stirring.

The reaction may be conducted at sub-ambient, ambient, or above ambient temperature, although ambient or above-ambient temperature is preferred. The reaction time is typically that required for completion or until a desired amount of product is formed. Generally, reaction time is between a few minutes and, for example, about 24-48 hours. Following the appropriate reaction time, the mixture is neutralized with an acid, such as 1N HCl. The product is then isolated by techniques well known in the art, such as filtration, solvent extraction, crystallization, chromatography, or distillation.

Examples of suitable solvents in which to the process of the invention can be conducted include alcohols such as methanol, ethanol, butanol, tert-butanol, isopropanol, and the like, polar aprotic solvents such as dimethylsulfoxide, dimethylformamide, N-methylpyrrolidinone, hexamethylphosphoroustriamide, dimethylacetamide, and the like.

Suitable bases for the process include tertiary amines such as trimethylamine, triethylamine, tripropylamine, tributylamine, and the like, metal hydroxides such as sodium hydroxide, potassium hydroxide, lithium hydroxide, and the like, or metal alkoxides such as sodium methoxide, sodium ethoxide, and the like. In addition, as noted above, the base can simply be the metal salt of the alkyl acetoacetate, such as sodium ethyl acetoacetate. The preferred base is the salt of the alkyl acetoacetate, triethylamine, or combinations of the two.

The activating agent is generally an acylating agent. Examples include ethyl chloroformate, methyl chloroformate, acetic anhydride, acetyl chloride, benzoyl chloride, and phenyl isocyanate. Ethyl choloroformate is preferred.

The alkyl acetoacetate used in the process of the invention is a compound of the formula III:

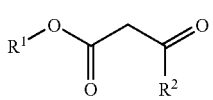

wherein $R^1$ is $C_1$-$C_8$ alkyl or cycloalkyl; and $R^2$ is $C_1$-$C_{12}$ alkyl, cycloalkyl, aryl, or aryl-$C_1$-$C_{12}$-alkyl-, each of which is optionally substituted with halogen or trifluoromethyl.

Preferably, $R^1$ is $C_1$-$C_6$ alkyl, more preferably $C_1$-$C_4$ alkyl. Preferred $R^1$ groups also include methyl, ethyl, and propyl, with ethyl being particularly preferred.

$R^2$ is preferably $C_1$-$C_6$ alkyl, more preferably $C_1$-$C_4$ alkyl. Preferred $R^2$ groups also include methyl, ethyl, and propyl, with methyl being particularly preferred.

As noted earlier, the alkyl acetoacetate may be used in the process of the invention as a salt. Examples include the sodium, potassium or lithium salts of the compound.

Preferred alkyl acetoacetate compounds include: ethyl acetoacetate and methyl acetoacetate, as well as metal salts of such alkyl acetoacetates such as sodium ethyl acetoacetate, potassium ethyl acetoacetate, lithium ethyl acetoacetate, sodium methyl acetoacetate, potassium methyl acetoacetate, and lithium methyl acetoacetate.

The nitroaryl compound of the invention is a generally of the formula II:

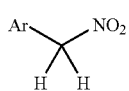

Preferably, Ar in formula II is phenyl optionally substituted with 1 or 2 halogen groups, such as chloro. Preferred nitroaryl compounds include phenylnitromethane, chlorophenylnitromethane, or dichlorophenylnitromethane.

The process of the invention provides compounds of formula I:

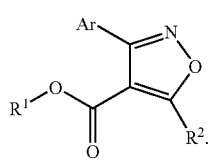

Preferred formula I compounds include those wherein $R^1$ and $R^2$ are independently $C_1$-$C_6$ alkyl, more preferably independently $C_1$-$C_4$ alkyl, and yet more preferably they are independently selected from methyl, ethyl, and propyl. Preferably, Ar in formula I is phenyl, optionally substituted with 1 or 2 halogen groups, such as chloro.

The compounds of formula I are useful precursors in the preparation of antibiotics and other biologically active compounds such as growth hormone secretagogue receptor antagonists, non-steroidal FXR agonists, adrenergic antagonists, as well as agricultural chemicals, and dye compounds.

"Alkyl," as used in this specification, whether alone or as part of another group (e.g., in dialkylamino), encompasses straight and branched chain aliphatic groups having the indicated number of carbon atoms. If no number is indicated, alkyl preferably has 1-14 carbon atoms, more preferably 1-10 carbon atoms, and further preferably 1-6 carbon atoms. Preferred alkyl groups include, without limitation, methyl, ethyl, propyl, isopropyl, butyl, isobutyl, sec-butyl, tert-butyl, pentyl, hexyl, heptyl, octyl, nonyl, decyl, and undecyl.

The term "cycloalkyl" as employed herein includes saturated and partially unsaturated cyclic hydrocarbon groups having 3 to 12 carbons, preferably 3 to 8 carbons. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a $C_6$-$C_{12}$ aromatic moiety comprising one to three aromatic rings. Preferably, the aryl group is a $C_6$-$C_{10}$ aryl group. Preferred aryl groups include, without limitation, phenyl and naphthyl. More preferred is phenyl. "Arylalkyl" or "aralkyl" refers to an aryl group attached to the parent molecular moiety through an alkyl group, as defined above.

The following examples are illustrative of the invention but are not intended to limit its scope.

EXAMPLES

Example 1

Ethyl 5-methyl-3-phenylisoxazole-4-carboxylate

To a 100-mL three-necked round-bottom flask fitted with stopper, a nitrogen purged inlet for a small diameter tube, and a gas outlet adaptor connected to a mineral oil bubbler is added sodium ethyl acetoacetate (Aldrich) (2.93 g, 19.8 mmol), dimethylsulfoxide (15 mL), and triethylamine (6 mL, 47.2 mmol). A slow nitrogen gas flow is started through the reactor. The mixture is stirred until the solid dissolves. A solution of phenylnitromethane (2.7 mL, 19.8 mmol), ethyl chloroformate (1.89 mL, 19.8 mmol) and tetrahydrofuran (5 mL) is prepared and added to a syringe attached to a syringe pump connected to the reactor using small bore tubing. This solution is then added to the reactor at a rate of 7 mL/hour with magnetic stirring of the reactor contents. After the addition is complete a sample is withdrawn, neutralized with excess 1N HCl (aq.), extracted with methylene chloride, and analyzed by gas chromatography. One major component is observed with a retention time the same as an authentic sample of ethyl 5-methyl-3-phenylisoxazole-4-carboxylate prepared by following a series of literature procedures (Journal of Medicinal Chemistry, 2000, Vol. 43, No. 16, p. 2971-2974 & Supporting Information for general procedure for preparation of chlorinated oxime using NCS)(Bioorganic & Medicinal Chemistry Letters 15 (2005) 1201-1204 for reaction of chlorinated oxime with sodium ethyl acetoacetate (prepared in situ) in methanol) and (Journal of Organic Chemistry p. 4305 (1962) for proton NMR data on desired product).

Example 2

Ethyl 5-methyl-3-phenylisoxazole-4-carboxylate

In a similar reaction as Example 1, the product is isolated by neutralization with excess 1N HCl(aq.) followed by extraction with methylene chloride and solvent removal. The resultant material is purified by column chromatography on silica gel using methylene chloride as eluting solvent. The product is then analyzed by NMR to confirm its identity. H-NMR (CDCl$_3$) 8.0-7.0 (m, 5H), 4.1 (q, 2H), 2.7 (s, 3H), 1.2 (t, 3H). Additionally the reaction mixture is analyzed by high resolution GC-MS to confirm the molecular formula of the product formed. The major component has a formula of $C_{13}H_{13}NO_3$ and a molecular weight of 231.09 g/mole consistent with ethyl 5-methyl-3-phenylisoxazole-4-carboxylate.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for preparing an isoxazole compound of the formula (I):

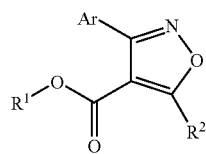

(I)

the process comprising:
contacting a nitroaryl of the formula (II):

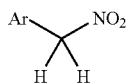

(II)

with an alkyl acetoacetate of the formula (III) or a salt thereof:

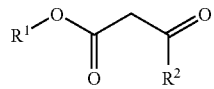

(III)

in the presence of an activating agent and a base, under conditions sufficient to provide the isoxazole compound, wherein
Ar is phenyl, naphthyl, or biphenyl, each of which is optionally substituted with 1, 2, or 3 groups independently selected from methyl, chloro, bromo, fluoro, iodo and trifluoromethyl;

$R^1$ is $C_1$-$C_8$ alkyl or cycloalkyl; and $R^2$ is $C_1$-$C_{12}$ alkyl, cycloalkyl, aryl, or aralkyl, each of which is optionally substituted with halogen or trifluoromethyl.

2. A process according to claim 1 wherein $R^1$ is $C_1$-$C_6$ alkyl.

3. A process according to claim 1 wherein $R^2$ is $C_1$-$C_6$ alkyl.

4. A process according to claim 1 wherein the alkyl acetoacetate of formula III is: ethyl acetoacetate, methyl acetoacetate, sodium ethyl acetoacetate, potassium ethyl acetoacetate, lithium ethyl acetoacetate, sodium methyl acetoacetate, potassium methyl acetoacetate, or lithium methyl acetoacetate.

5. A process according to claim 1 wherein Ar is phenyl optionally substituted with 1 or 2 halogen groups.

6. A process according to claim 1 wherein the nitroaryl compound of formula II is phenylnitromethane, chlorophenylnitromethane, or dichlorophenylnitromethane.

* * * * *